US012226403B2

(12) United States Patent
Jain et al.

(10) Patent No.: US 12,226,403 B2
(45) Date of Patent: Feb. 18, 2025

(54) TEBIPENEM PIVOXIL IMMEDIATE AND MODIFIED RELEASE ORAL DOSAGE FORMS (71) Applicant: SPERO THERAPEUTICS, INC., Cambridge, MA (US)

(72) Inventors: Akash Jain, Cambridge, MA (US); Enxian Lu, Shanghai (CN); Shaoqiong Lyu, Shanghai (CN); Shoufeng Li, North Brunswick, NJ (US); Timothy Keutzer, Cambridge, MA (US); Luke Utley, Cambridge, MA (US); Grazyna Fraczkiewicz, Lancaster, CA (US); Joyce MacWan, Lancaster, CA (US)

(73) Assignee: SPERO THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 16/470,058

(22) PCT Filed: Dec. 15, 2017

(86) PCT No.: PCT/US2017/066729
§ 371 (c)(1),
(2) Date: Jun. 14, 2019

(87) PCT Pub. No.: WO2018/112372
PCT Pub. Date: Jun. 21, 2018

(65) Prior Publication Data
US 2020/0016126 A1 Jan. 16, 2020

Related U.S. Application Data (60) Provisional application No. 62/434,643, filed on Dec. 15, 2016, provisional application No. 62/438,071, filed on Dec. 22, 2016.

(51) Int. Cl.
*A61K 9/16* (2006.01)
*A61K 9/00* (2006.01)
*A61K 9/20* (2006.01)
*A61K 9/28* (2006.01)
*A61K 31/427* (2006.01)

(52) U.S. Cl.
CPC .......... *A61K 31/427* (2013.01); *A61K 9/0053* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2846* (2013.01)

(58) Field of Classification Search
CPC ................................ A61K 9/16; A61K 31/427
See application file for complete search history.

(56) References Cited

U.S. PATENT DOCUMENTS

| 4,851,230 A * | 7/1989 | Tencza ...................... A61J 3/10 424/467 |
| 5,534,510 A | 7/1996 | Abe et al. |
| 5,886,172 A | 3/1999 | Abe et al. |
| 2004/0037883 A1* | 2/2004 | Zhou .................... A61K 31/135 424/471 |
| 2006/0099253 A1* | 5/2006 | Becker .................... A61P 31/04 514/192 |
| 2008/0069879 A1 | 3/2008 | Bhiwgade et al. |
| 2011/0118229 A1* | 5/2011 | Choi ...................... A61P 31/04 540/350 |
| 2020/0055857 A1 | 2/2020 | Jain et al. |
| 2022/0142986 A1 | 5/2022 | Jain et al. |

FOREIGN PATENT DOCUMENTS

| CN | 102558181 A | 7/2012 |
| CN | 102836130 A | 12/2012 |
| CN | 102276611 B | 1/2013 |
| CN | 102860985 B | 1/2013 |
| CN | 102885811 B | 1/2013 |
| CN | 102952125 A | 3/2013 |
| CN | 103054815 A | 4/2013 |
| CN | 103371977 A * | 10/2013 |
| CN | 103655483 A | 3/2014 |
| CN | 103664949 A | 3/2014 |
| CN | 104013583 A | 9/2014 |
| CN | 104027310 A | 9/2014 |
| CN | 104224725 A | 12/2014 |
| CN | 103664948 B | 12/2015 |
| CN | 105193742 A | 12/2015 |

(Continued)

OTHER PUBLICATIONS

Bassetti et al (Development of novel antibacterial drugs to combat multiple resistant organisms; Langerbecks Arch Surg (2015) 400: 153-165) (Year: 2015).*
Bassetti et al (development of Novel Antibacterial Drugs to Combat Multiple Resistant Organisms; Langerbescks Arch Surg, 400: 153-165, 2015) (Year: 2015).*
International Search Report; International Application No. PCT/US2017/066729; International Filing Date—Dec. 15, 2017; Date of Mailing—Apr. 24, 2018; 6 pages.
Nakashima et al., "Effect of Probenecid or Diet on Tebipenem Pivoxil Tablets Pharmacokinetics in Healthy Male Volunteers," Mar. 2009, Japanese Journal of Chemotherapy, Japan Society of Chemotherapy, vol. 57, No. Suppl. 1, 6 pages.
Written Opinion; International Application No. PCT/US2017/066729; International Filing Date—Dec. 15, 2017; Date of Mailing—Apr. 24, 2018; 9 pages.

(Continued)

Primary Examiner — Micah Paul Young
(74) Attorney, Agent, or Firm — CANTOR COLBURN LLP (57) ABSTRACT

Immediate and modified release oral dosage forms of tebipenem pivoxil including dosage form cores are provided. The dosage form core includes tebipenem pivoxil in free base or salt form, and excipients including a binder, a lubricant, optionally a diluent, and optional additional excipients. The weight to weight ratio of tebipenem pivoxil to the excipients in the dosage form core is from 30:60 to 60:30. The disclosure includes methods of treating bacterial infections including complicated urinary tract infections.

16 Claims, 7 Drawing Sheets

(56) References Cited

FOREIGN PATENT DOCUMENTS

| | | | |
|---|---|---|---|
| CN | 105963261 A | | 9/2016 |
| CN | 105997891 A | * | 10/2016 |
| CN | 107737107 B | | 5/2020 |
| EP | 0632039 A1 | | 4/1995 |
| JP | H853453 A | | 2/1996 |
| JP | 08256296 A | | 10/1996 |
| JP | H10195076 A | | 7/1998 |
| JP | 3317604 B2 | | 8/2002 |
| JP | 3317649 B2 | | 8/2002 |
| JP | 2003171277 A | | 6/2003 |
| JP | 2004035517 A | | 2/2004 |
| JP | 2004035518 A | | 2/2004 |
| JP | 2011504495 A | | 2/2011 |
| KR | 20090103227 A | | 10/2009 |
| WO | WO-2007070164 A1 * | 6/2007 | ............ A61K 31/44 |
| WO | 2012079504 A1 | | 6/2012 |
| WO | 2012139424 A1 | | 10/2012 |
| WO | 2018112372 A1 | | 6/2018 |
| WO | 2018145089 A1 | | 8/2018 |

OTHER PUBLICATIONS

Nakashima et al., "Pharmacokinetics and Safety of Oral Carbapenem Antibiotic Tebipenem Pivoxil Tablets in Healthy Male Volunteers," Japanese Journal of Chemotherapy, (2009), vol. 57, No. Suppl. 1, pp. 82-89.

Hazra, S. et al., "Tebipenem, a New Carbapenem Antibiotic, Is a Slow Substrate That Inhibits the β-Lactamase from *Mycobacterium tuberculosis*," Biochemistry, May 20, 2014; vol. 53, No. 22, pp. 3671-3678.

International Preliminary Report on Patentability and Written Opinion of International Application No. PCT/US2017/066729; International Filing Date—Dec. 15, 2017; Date of Issuance—Jun. 18, 2019, 9 pages.

Muratani, et al., "Antimicrobial Activity of Tebipenem Against Various Clinical Isolates from Various Specimen, Mainly Urinary Tract," The Japanese Journal of Antibiotics; Apr. 1, 2009, vol. 62, No. 2, pp. 116-126.

Hikida et al., "In Vitro Antibacterial Activity of LJC 11,036, an Active Metabolite of L-084, a New Oral Carbapenem Antibiotic With Potent Antipneumococcal Activity," Antimicrobial Agents and Chemotherapy, (1999), vol. 43, (No. 8), 2010-2016.

Nakashima et al., "Effect of Probenecid or Diet on Tebipenem Pivoxil Tablets Pharmacokinetics in Healthy Male Volunteers," Hamamatsu Institute of Clinical Pharmacology & Therapeutics, (2009), vol. 57, (No. 1), 103-108.

Jain et al., "Tebipenem, the First Oral Carbapenem Antibiotic," Expert Review of Anti-Infective Therapy, Taylor & Francis Group, (2018), 1-11.

Nakashima et al. "Pharmacokinetics and Safety of Oral Carbapenem Antibiotic Tebipenem Pivoxil Tablets in Healthy Male Volunteers," Jpn. J. Chemother., (2008), vol. 57 (S-1), 82-89.

Aitipamula, et al. "Polymorphism: Fundamentals and Applications," Supramolecular Chemistry: From Molecules to Nanomaterials, John Wiley & Sons, Ltd., (2012), 1-18.

Extended European Search Report for EP Application No. 22160275.8-1109; Dated—Jun. 28, 2022; 85 pages.

International Search Report; International Application No. PCT/US2021/059178; International Filing Date—Nov. 12, 2021; Date of Mailing—Apr. 22, 2022; 5 pages.

Written Opinion of the International Searching Authority for International Application No. PCT/US2021/059178; International Filing Date—Nov. 12, 2021; Date of Mailing—Apr. 22, 2022; 8 pages.

Aitipamula et al., "Polymorphism: Fundamentals and Applications," Supramolecular Materials Chemistry, Wiley Online Library, (2012), Abstract, one page.

Li et al., "Lubricants in Pharmaceutical Solid Dosage Forms," Lubricants ISSN 2075-4442, www.mdpi.com/journal/lubricants, (2014), vol. 2, 21-43.

Yao et al., "Antibacterial Properties of Tebipenem Pivoxil Tablet, a New Oral Carbapenem Preparation Against a Variety of Pathogenic Bacteria in Vitro and in Vivo," Molecules, (2016), vol. 21, (No. 62), 1-14.

International Preliminary Report on Patentability; International Application No. PCT/US2021/059178; International Filing Date—Nov. 12, 2021; Date of Mailing—May 16, 2023; 8 pages.

Tanaka et al., "Tebipenem in Vitro," Journal of the Japanese Society of Chemotherapy, (2009), vol. 57, (No. S-1), 30-37.

Yamada et al. "Tebipenem in Vitro," Journal of the Japanese Society of Chemotherapy, (2009), vol. 57, (No. S-1), 1-14.

* cited by examiner

TEBIPENEM PIVOXIL IMMEDIATE AND MODIFIED RELEASE ORAL DOSAGE FORMS

CROSS REFERENCE TO RELATED APPLICATIONS

This application is a National Stage application of PCT/US2017/066729, filed Dec. 15, 2017. This application claims priority to U.S. Provisional Patent Application No. 62/434,643, filed Dec. 15, 2016, and to U.S. Provisional Application No. 62/438,071, filed Dec. 22, 2016, the entire contents of which are incorporated herein by reference.

FIELD OF THE DISCLOSURE

Immediate and modified release tebipenem pivoxil oral dosage form cores and oral dosage forms are provided by this disclosure. Methods of treating a urinary tract infection in a patient with an immediate or modified release oral dosage form of this disclosure are also included.

BACKGROUND

Tebipenem pivoxil is an orally-administered pivaloyloxymethyl prodrug of Tebipenem, an antibiotic from the carbapenem subgroup of β-lactam antibiotics:

tebipenem pivoxil

Tebipenem pivoxil has been developed to treat severe bacterial infections that have acquired antibiotic resistance to commonly used anti-infective medicines. Following oral administration, the ester and acetal bonds of the prodrug are cleaved to release active tebipenem.

While the prodrug has high solubility in gastrointestinal (GI) simulated fluids, it readily decomposes at pH 1 and pH 9 and is sensitive to oxidative conditions.

Thus, stable tebipenem pivoxil dosage forms having consistent and desirable physical and chemical properties are needed. This disclosure provides dosage forms that meet this need and have additional advantages which are described in the disclosure.

SUMMARY

This disclosure provides immediate and modified release oral dosage forms of tebipenem pivoxil. The disclosure provides immediate and modified release solid oral dosage form comprising a dosage form core, wherein the dosage form core comprises: tebipenem pivoxil or a pharmaceutically acceptable salt thereof and excipients including a binder, a lubricant, an optionally a diluent.

The disclosure provides an immediate release solid oral tebipenem pivoxil dosage form, which provides an in vitro release of greater than 85% of the tebipenem pivoxil in 15 minutes when measured by the USP Paddle method at 50 rpm in 900 mL of 50 mM acetate buffer, pH 5.0 at 37° C.

The disclosure also provides a modified release solid oral tebipenem pivoxil dosage form, which provides an in vitro release of NMT (not more than) 50% of the tebipenem pivoxil after 30 minutes when measured by the USP Paddle method at 50 rpm in 900 mL of 50 mM acetate buffer, pH 5.0 at 37° C. In certain embodiments this modified release dosage form releases releases NLT (not less than) 85% of the total tebipenem pivoxil after 4 hours, when measured by the USP Paddle method at 50 rpm in 900 mL of 50 mM acetate buffer, pH 5.0 at 37° C.

This disclosure also provides a short modified release solid oral tebipenem pivoxil dosage form, which provides an in vitro release of NMT (not more than) 50% of the tebipenem pivoxil after 30 minutes when measured by the USP Paddle method at 50 rpm in 900 mL of 50 mM acetate buffer, pH 5.0 at 37° C. In certain embodiments this modified release dosage form releases releases NLT (not less than) 85% of the total tebipenem pivoxil after 2 hours, when measured by the USP Paddle method at 50 rpm in 900 mL of 50 mM acetate buffer, pH 5.0 at 37° C.

The disclosure also provides a method of treating a bacterial infection in a patient comprising administering an oral dosage form of the disclosure to the patient. In certain embodiments the bacterial infection is a urinary tract infection, including a complicated urinary tract infection.

BRIEF DESCRIPTION OF THE DRAWINGS

The above and other aspects and features of the present disclosure will become more apparent by describing exemplified embodiments thereof in detail with reference to the attached drawings, in which.

DETAILED DESCRIPTION

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or language indicating an example (e.g., "such as"), is intended merely for illustration and does not pose a limitation on the scope of the invention unless otherwise claimed. No language in the specification should be construed as indicating any non-claimed element as essential to the practice of the invention.

The terms "a" and "an" do not denote a limitation of quantity, but rather denote the presence of at least one of the referenced item.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe are included in the value. Thus compositions slightly outside the cited ranges are also encompassed by the scope of the present claims.

The terms "comprising," "including," and "containing" are non-limiting. Other non-recited elements may be present in embodiments claimed by these transitional phrases. Where "comprising," "containing," or "including" are used as transitional phrases other elements may be included and still form an embodiment within the scope of the claim. The open-ended transitional phrase "comprising" encompasses the intermediate transitional phrase "consisting essentially of" and the close-ended phrase "consisting of."

The term "immediate release" refers to a solid dosage form that release the active ingredient, tebipenem pivoxil, immediately after oral administration.

The term "modified release" refers to a solid oral dosage form that permits the release of the active ingredient, tebipenem pivoxil, over an extended period of time relative to the time for the immediate release formulation to release the active agent, to maintain therapeutically effective plasma levels. The modified release formulation may be a controlled release formulation, one that exhibits substantially zero order release kinetics. It may also be a sustained release formulation, which exhibits first order kinetics.

"Pharmaceutically acceptable salts" includes derivatives of tebipenem pivoxil, wherein the tebipenem pivoxil is modified by making acid or base addition salts thereof, and further refers to pharmaceutically acceptable solvates, including hydrates, and co-crystals of such compounds and such salts. Examples of pharmaceutically acceptable salts include, but are not limited to, mineral or organic acid addition salts of basic residues such as amines; alkali or organic addition salts of acidic residues; and the like, and combinations comprising one or more of the foregoing salts. The pharmaceutically acceptable salts include non-toxic salts and the quaternary ammonium salts of the active agent, tebipenem pivoxil. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; and combinations comprising one or more of the foregoing salts; organic amine salts such as triethylamine salt, pyridine salt, picoline salt, ethanolamine salt, triethanolamine salt, dicyclohexylamine salt, N,N' dibenzylethylenediamine salt, and the like; and amino acid salts such as arginate, asparginate, glutamate, and the like; and combinations comprising one or more of the foregoing salts. All forms of tebipenem pivoxil are included in the disclosure, including all crystalline, amorphous, and polymorph forms.

When a weight of tebipenem pivoxil that may be in a salt form is given the value refers to the amount of tebipenem pivoxil rather than the weight of tebipenem pivoxil salt. For example, 500 mg of tebipenem pivoxil, where the tebipenem pivoxil is a hydrobromide salt, indicates that 581.2 g of tebipenem pivoxil hydrobromide are present. Unless it is clear from the context that tebipenem pivoxil free base is intended or tebipenem pivoxil free base is explicitly specified the term "tebipenem pivoxil" includes tebipenem pivoxil free base and the pharmaceutically acceptable salts of tebipenem pivoxil, for example tebipenem pivoxil HBr.

Dosage Form Composition

New tebipenem pivoxil immediate and modified release solid dosage forms have been developed. The dosage forms may be a capsule, a granule, a tablet core, a powder, but are not limited thereto. The dosage forms have a core including tebipenem pivoxil as an active ingredient and one or more excipients. While the tebipenem pivoxil dosage forms may contain a range of tebipenem pivoxil, for example, from 100 to 1,200 milligrams (mg) or 100 to 600 mg of tebipenem pivoxil, tablets containing 100 mg, 300 mg, and 500 mg of tebipenem pivoxil are exemplified.

The disclosure provides immediate or modified release solid oral dosage forms comprising a dosage form core, wherein the dosage form core comprises: tebipenem pivoxil or a pharmaceutically acceptable salt thereof and excipients including a binder, a lubricant, an optionally a diluent. The weight to weight ratio of tebipenem pivoxil (as free base) to the excipients in the core is from 30:60 to 60:30, or in some embodiments from 30:45 to 45:30, or about 50:50, or about 30:40.

The disclosure includes tebipenem pivoxil immediate and modified release oral dosage forms, such as a tablet dosage forms.

The tebipenem pivoxil dosage forms of this disclosure have a number of desirable properties. For example certain of the new modified release dosage forms are effective for at least 6 hours, permitting less frequent administration than immediate release form and in some embodiment permitting twice a day administration. The modified release tebipenem pivoxil dosage exhibit a lower plasma $C_{max}$ and higher plasma $C_{min}$ than previous dosage forms resulting in an increased duration of the effective concentration, increased efficacy, increased duration of effect as compared to immediate dosage forms. Once released, the modified release dosage form provides high absorption of the tebipenem pivoxil from the digestive tract. The modified release tebipenem pivoxil dosage forms of this disclosure reaches plasma $C_{max}$ 1 to 4 hours after oral administration, in certain embodiments the modified release tebipenem pivoxil dosage forms of the disclosure reach plasma $C_{max}$ 2 to 4 hours after oral administration, and in other embodiments the modified release tebipenem pivoxil dosage forms of this disclosure reaches plasma $C_{max}$ 1 to 2.5 hours after oral administration.

The new immediate release tebipenem pivoxil dosage form is very quickly soluble in water or an aqueous solution and also provides high absorption of the tebipenem pivoxil from the digestive tract. Thus, the immediate release dosage form provides rapid onset of drug action and rapid therapeutic benefit. The immediate release tebipenem pivoxil dosage form of this disclosure reaches plasma $C_{max}$ within 0.5-2 hours or 0.5 to 1.5 hours after oral administration. When the HBr salt is used the immediate release dosage form of this disclosure reaches plasma $C_{max}$ in less than 1.5 hours.

The immediate and modified release tebipenem pivoxil dosage form has a shelf stability of at least 12 months and preferably at least 24 months at room temperature.

The immediate and modified release tebipenem pivoxil dosage forms have dissolution profiles that are independent of dosage strength from 100 to 1000 mg of tebipenem pivoxil.

In certain embodiments the modified release tebipenem pivoxil dosage form provides an in vivo plasma $T_{max}$ of 3 to 8, 3 to 6, or 3 to 4 hours after administration. In certain embodiments the short modified release tebipenem pivoxil dosage form provides an in vivo plasma $T_{max}$ of 0.5 to 4, 1 to 3, or 1 to 2.5 hours after administration.

The disclosure includes tebipenem pivoxil tablet formulations in which at least 30%, at least 40%, at least 45%, at least 50%, at least 55%, at least 60%, or at least 65% of the tablet by weight is tebipenem pivoxil. The disclosure includes tebipenem pivoxil dosage forms in which tebipenem pivoxil is 30% to 70% or 40% to 60% by weight of the tablet core and the excipients include 70% to 30% or 60% to 40% by weight of the tablet core. In certain embodiments the tebipenem pivoxil includes 45% to 55% by weight of the tablet core and the excipients include 55% to 45% by weight of the tablet core. In some other embodiments, tebipenem pivoxil includes 50% of the tablet core and the excipients include 50% of the tablet core. In some embodiments the tebipenem pivoxil includes 40% of the tablet core.

The excipients include, but are not limited to, one or more of a binder, a release control agent, a disintegrant, a diluent, or a lubricant. The excipients may further include a glidant, a solvent, a viscosity agent, an emulsifier, a buffer, a bulking agent, a coloring agent, a taste-improving agent, a flow agent, an absorbent, but are not limited thereto.

The disclosure includes dosage cores and coated tablets containing a binder. For example, the binder may be microcrystalline cellulose, silicified microcrystalline cellulose, ethyl cellulose, lactose, starch, gelatin, or any combination of any two of the foregoing. The binder may be present in the tablet core or coated tablet in an amount (% w/w) from 1% to 50% or from 5% to 40%, or from 10% to 20%, or 15%. In certain embodiments, Avicel PH102, a type of microcrystalline cellulose, is the binder.

The disclosure includes modified release oral dosage forms, including dosage cores and coated tablets containing a release control agent. A release control agent is an agent that assists in delivery of the active ingredient over a desired period of time. The release control agent may be present in the tablet core or coated tablet in an amount (% w/w) from 1% to 50% or from 5% to 40%, or from 10% to 20%, or 15%. In certain embodiments hydroxypropyl methylcellulose (HPMC) is included as a release control agent. K grade HPMC products have a methoxyl degree of substitution of 1.4, approximately 22% methoxyl content, and hydroxypropyl content of approximately 8.1%. E grade HPMC products have a methoxyl degree of substitution of 1.9, approximately 29% methoxyl content, and approximately 8.5% hydroxypropyl content. HPMC K4M is used as a release control agent in some modified release tebipenem pivoxil dosage forms of this disclosure. In certain embodiments the HPMC K4M is a hydroxypropyl methyl cellulose with a particle size range of 170 to 250 micrometers and a viscosity range of 2700 to 5050 cps at 40° C. or about 4000 mPa·s at 2% in water at 20° C. HPMC E50 LV and HPMC E3 are also used as a release control agents in some embodiments of this disclosure. HPMC E50 LV has viscosity of 35-65 cps at 40° C. or about 50 mPa·s at 2% in water at 20° C., and HPMC E3 and has a viscosity of about 3 mPa·s at 2% in water at 20° C. In certain embodiments such as the 2 hr modified release dosage form the suitable release control agent is polyvinylpyrrolidone such as PVP K12, which has an average molecular weight of 3500-6000 and is slightly (5%) water soluble. Other suitable release control agents include hydroxypropyl methylcellulose, hydroxypropyl cellulose, hypromellose acetate succinate, polyvinylpyrrolidone, and copovidone.

The disclosure includes dosage cores and coated tablets containing a diluent. For example, the diluent may be starch, sucrose, monohydrate lactose, mannitol, sorbitol, or any combination of any two of the foregoing. The diluent may be present in the tablet core or coated tablet in an amount (% w/w) from 1% to 50% or from 5% to 40%, or from 10% to 20%, or 15%. In some embodiments the diluents are monohydrate lactose and mannitol.

The disclosure includes dosage forms, including dosage form cores and coated tablets containing a disintegrant. For example, the disintegrant may be croscarmellose sodium, crospovidone (also called copovidone), sodium starch glycolate, or any combination of any two or more of the foregoing. The disintegrant may be present in the tablet core or coated tablet in an amount (% w/w) from 1% to 50% or from 5% to 40%, or from 10% to 20%, or 15%. In some embodiments PVPP XL-10, a type of crospovidone, is the disintegrant. PVPP XL-10 is a crosslinked polyvinylpyrrolidone having an average particle size of 30 μm. Other suitable disintegrants include croscarmellose sodium, pregelatinized starch, sodium starch glycolate, mannitol, maize starch, potato starch, alginic acid, and wheat starch.

The disclosure includes dosage cores and coated tablets containing a lubricant. The kind and amount of lubricant are not limited so long as within the ranges acceptable for pharmaceutical use. For example, the lubricant may be a fatty acid ester, stearic acid, magnesium stearate, glyceryl behenate, calcium stearate, sodium stearyl fumarate, sodium lauryl sulfate, magnesium lauryl sulfate, sodium benzoate, talc, hydrogenated oil, Carnauba wax, or a combination of any two of the foregoing. The lubricant may be present in the tablet core or coated tablet in an amount (% w/w) from 0.1% to 5%, 0.1% to 2.0%, or from 0.1% to 1.0%, or from 0.25% to 0.5%, or 0.375%. In certain embodiments the lubricant is magnesium stearate.

In an embodiment, the tablet core may be a modified release tablet core, which includes tebipenem pivoxil as an active ingredient, hydroxypropyl methyl cellulose as a release control agent, mannitol as a diluent, microcrystalline cellulose as a binder, and magnesium stearate as a lubricant. For example, the table core may include 40 to 60 weight percent of tebipenem pivoxil, 10 to 30 weight percent hydroxypropyl methyl cellulose, 10 to 20 weight percent mannitol, 10 to 20 weight percent microcrystalline cellulose, and 0.1 to 5 weight percent magnesium stearate.

Figure 7:
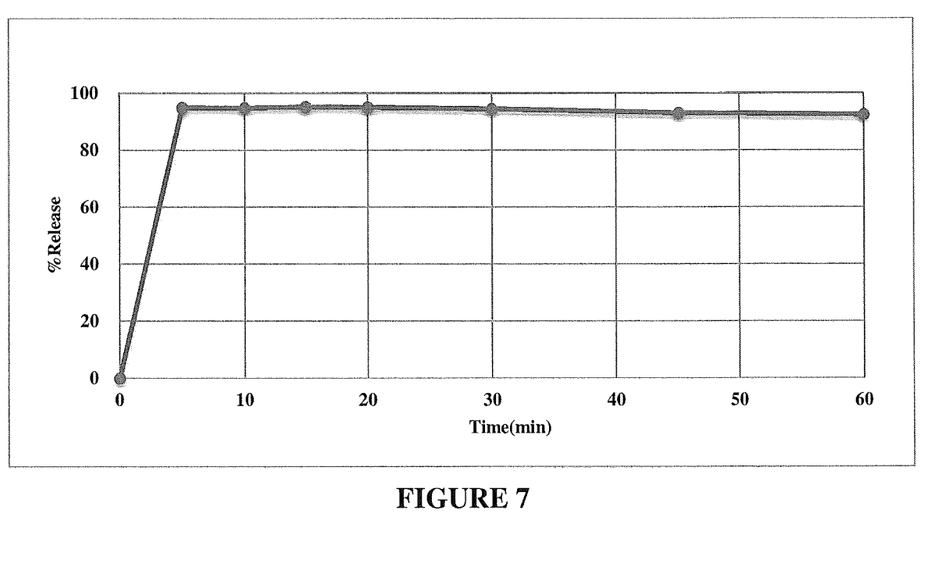
FIG. 7 shows a dissolution profile of a 300 mg tebipenem pivoxil immediate release uncoated tablet core at pH 5. The formulation of the modified release dosage form is provided in Table 11B.

The immediate release tebipenem pivoxil tablet core can release at least 80%, at least 85%, at least 90%, or at least 95% of the total amount of tebipenem pivoxil in a pH 5.0 buffer at 37° C. with a paddle speed of 50 revolutions per minute (rpm) in 30 minutes, in 15 minutes, or in 10 minutes. In certain embodiments the immediate release tebipenem pivoxil tablet core can release at least 95% of the total amount of tebipenem pivoxil in a pH 5.0 buffer at 37° C. with a paddle speed of 50 revolutions per minute (rpm) in 15 minutes. The immediate release tebipenem pivoxil tablet core may release tebipenem pivoxil substantially as shown in the dissolution profile of FIG. 1 of FIG. 7, when the tebipenem pivoxil is in the form of tebipenem pivoxil HBr.

Figure 2:
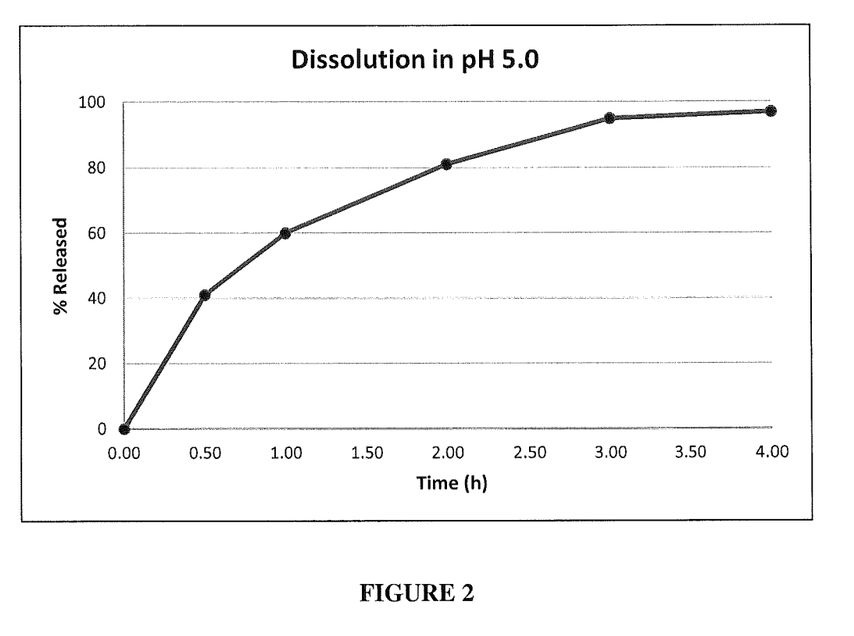
FIG. 2 shows a dissolution profile of a 500 mg tebipenem pivoxil modified release uncoated tablet core at pH 5. The formulation of the modified release dosage form is provided in Example 3.
Figure 8:
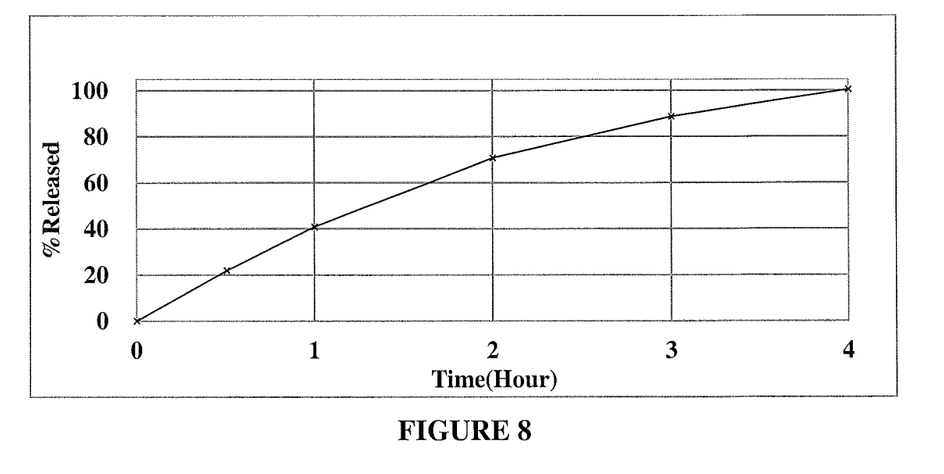
FIG. 8 shows a dissolution profile of a 300 mg tebipenem pivoxil modified release uncoated tablet core at pH 5. The formulation of the modified release dosage form is provided in Table 12B.

The modified release tebipenem pivoxil tablet core can release between 30% and 50%, or between 35% and 45%, or NMT than 50% of the total amount of tebipenem pivoxil after 30 minutes in a pH 5.0 buffer at 37° C. with a paddle speed of 50 revolutions per minute (rpm). The modified release tebipenem pivoxil tablet core can release between 50% and 70%, or between 55% and 65%, of the total amount of tebipenem pivoxil after 60 minutes in a pH 5.0 buffer at 37° C. with a paddle speed of 50 revolutions per minute (rpm). The tebipenem pivoxil tablet core may also release NLT 85%, or NLT 90%, of the total amount of tebipenem pivoxil after 4 hours in a pH 5.0 buffer at 37° C. with a paddle speed of 50 rpm. The modified release tablet core may release tebipenem pivoxil substantially as shown in the dissolution profile of FIG. 2 of FIG. 8 (for the HBr salt formulation disclosed in Table 12B).

Coatings

The dosage form may further include a coating.

In certain embodiments the coating is an enteric coating. Such coatings are insoluble at the acidic pH of gastric fluid, for example less than pH 3, but readily soluble at the neutral or nearly neutral pH of the gastrointestinal tract, for example at pH 6.8 to pH 7.4.

The tebipenem pivoxil dosage form core may be coated with an enteric coating, such as an immediate release or modified release enteric coating, to form an enteric coated dosage form. An enteric coating is designed to be resistant to stomach acid, and will not dissolve until the tablet reaches the small intestine. The pH dependent coating can protect an acid-sensitive tebipenem pivoxil from the low pH of gastric fluid. When the enteric coated tebipenem pivoxil dosage form reaches the neutral environment of the intestine, its active ingredients are then dissolved and become available for absorption into the bloodstream. In an embodiment, an enteric coating may be a polymer applied on the tebipenem pivoxil core. The polymer may be selected from a poly (acrylate), a poly(methacrylate), a methyl acrylate-methacrylic acid copolymer, a methyl methacrylate-methacrylic acid copolymer, shellac, cellulose acetate phthalate (CAP), cellulose acetate succinate, hydroxypropyl methyl cellulose phthalate, hydroxypropyl methyl cellulose acetate succinate (hypermellose acetate succinate), polyvinyl acetate phthalate (PVAP), cellulose acetate trimellitate, sodium alginate, zein, and a combination thereof. The enteric coating may further include a base such as an alkali metal hydroxide, an alkali metal carbonate, an alkali metal hydrocarbonate, a combination thereof, but is not limited thereto.

In certain embodiments the immediate release enteric coating comprises a poly(methacrylate) and a base. In an embodiment, the base can be a metal hydroxide, for example, sodium hydroxide or potassium hydroxide. In another embodiment, the base can be a metal carbonate, for example, sodium carbonate or potassium carbonate, or a metal hydrocarbonate, for example, sodium hydrocarbonate or potassium hydrocarbonate. Other suitable coatings include polyvinyl alcohol, certain grades of hydroxylpropyl methylcellulose, and mixtures of HPMC and polyethylene glycol (PEG). The coating may additionally include a plasticizer. However, the immediate release coating is not limited thereto and any conventional coating that is insoluble at low pH (pH less than about 3) but that will immediately releasing the active ingredient at neutral or basic pH can also be used. The immediate release enteric coating may have a thickness of about 20 micrometers to about 100 micrometers. The weight gain of the coating can be from about 0.1 to 100% weight gain based on the weight of the tablet core, or about 2 to about 75%, about 2 to about 50%, about 2% to about 15%, about 2% to about 10%, or about 4% to about 8%.

The coating can be an immediate release coating or in some embodiments the coating is a modified release coating. Suitable coatings include hypromellose or hypromellose USP also known as hydroxypropyl methylcellulose (HPMC). HPMC is a water soluble excipient that may be used film coating agent, although certain grades of HPMC are more commonly used as binders. PHARMACOAT (ShinEtsu Chemical-Co., Ltd.). PHARMACOAT 603 is a hypermellose grade having substitution type 2910 and a labeled viscosity of 3 mPa-s that is suitable for use as a film coating. The OPADRY tradename is used for a variety of pharmaceutical coatings, and includes immediate release coatings comprised primarily of HPMC (hydroxypropyl methyl cellulose or hypromellose) or PVA (polyvinyl alcohol) and PEG (polyethylene glycol). PEG may be used as a plasticizer in OPADRY coatings. EUDRAGITs, such as EUDRAGIT L 100-55, are another suitable class of coatings. EUDRAGITs are copolymers derived from esters of acrylic and methacrylic acid, with additional functional groups in some cases.

The coating may include additional excipients such as film formers, printing inks, buffering agents, pH adjusters, preservatives, dyes, and flavors. In some instances, a single material will include any two or more of any of the foregoing excipients.

An amount of tebipenem pivoxil in the uncoated tablet may be 100 mg and the uncoated tablet weight may be 200 mg. In another example, an amount of tebipenem pivoxil in the uncoated tablet may be 500 mg and the uncoated tablet weight may be 1,000 mg. In another example the weight of tebipenem pivoxil HBr in the uncoated tablet may be 348.9 mg, the weight of tebipenem pivoxil in the uncoated tablet may be 300 mg, and the total weight of the uncoated tablet may be 750 mg. A thickness of the 500 mg tablet may be from 5.00 to 8.00 millimeters (mm), or from 6.00 to 7.00 mm, or from 6.50 to 7.00 mm, or from 6.75 to 7.00 mm. An amount of the coating of the tablet is from 1 to 5 weight percent of the total weight of the tablet, for example, from 2 to 3 weight percent of the total weight of the tablet.

Embodiments may be combined only so long as a stable solid formulation or its core results. "A combination of any of the foregoing" only includes combinations that results in a stable tablet or tablet core.

Methods of Treatment

The disclosure includes a method of treating a bacterial infection in a subject by administering a dosage form the disclosure to a subject at risk for a bacterial infection or suffering from a bacterial infection.

Treatment of human patients is particularly contemplated. However, treatment of non-human subjects, such as livestock or companion animals, is within the scope of the disclosure.

In some embodiments, the bacterial infection or antibiotic-tolerant or antibiotic-resistant infection is caused by a Gram-negative bacterium.

The extended release tebipenem pivoxil oral dosage form of this disclosure may be administered alone, so that tebipenem pivoxil is the only active agent administered to the subject or the dosage form may be administered in combination with one or more additional active agents. Combination administration includes concurrent or sequential administration of active agents.

In an embodiment of any of the methods of this disclosure, the microbial infection is the result of a pathogenic bacterial infection. Examples of pathogenic bacteria include, without limitation, bacteria within the genera *Aerobacter, Aeromonas, Acinetobacter, Agrobacterium, Bacillus, Bacteroides, Bartonella, Bordetella, Brucella, Burkholderia, Calymmatobacterium, Campylobacter, Citrobacter, Clostridium, Corynebacterium, Enterobacter, Enterococcus, Escherichia, Francisella, Fusobacterium, Haemophilus, Hafnia, Helicobacter, Klebsiella, Legionella, Listeria, Morganella, Moraxella, Porphyromonas, Proteus, Providencia, Pseudomonas, Salmonella, Serratia, Shigella, Staphylococcus, Streptococcus, Treponema, Xanthomonas, Vibrio,* and *Yersinia*. Specific examples of such bacteria include *Vibrio harveyi, Vibrio cholerae, Vibrio parahemolyticus, Vibrio alginolyticus, Pseudomonas phosphoreum, Pseudomonas aeruginosa, Yersinia enterocolitica, Escherichia coli, Salmonella typhimurium, Haemophilus influenzae, Helicobacter pylori, Bacillus subtilis, Borrelia burgdorferi, Neisseria meningitidis, Neisseria gonorrhoeae, Yersinia pestis, Campylobacter jejuni, Mycobacterium tuberculosis, Enterococcus faecalis, Streptococcus pneumoniae, Streptococcus pyogenes, Klebsiella pneumoniae, Burkholderia cepacia, Acinetobacter baumannii, Staphylococcus epidermidis,* and *Staphylococcus aureus*.

In some embodiments, the Gram-negative bacterium is a *Pseudomonas*, e.g., *P. aeruginosa, Burkholderia,* or an *Acinetobacter*, e.g., *A. baumannii*.

In some embodiments, the Gram-negative bacterium is an Enterobacteriaceae, e.g., *Klebsiella pneumonia,* e.g., *Escherichia coli,* e.g., *Enterobacter cloacae,* e.g., *Serratia marcescens,* e.g., *Salmonella typhimurium,* e.g., *Shigella dysenteriae,* e.g., *Proteus mirabilis,* e.g., *Citrobacter freundii,* e.g., *Yersinia pestis*.

In some embodiments, the infection is a polymicrobial infection, e.g., an infection comprising more than one organism. In some embodiments, the infection comprises at least one of the organisms listed above, e.g., one or more of *Pseudomonas*, e.g., *P. aeruginosa, Klebsiella,* e.g., *Klebsiella pneumoniae,* and/or *Acinetobacter,* e.g., *A. baumannii*.

In some embodiments, the methods further include administering an additional active agent in combination the modified release solid dosage form the disclosure, such as an antibiotic selected from the group consisting of but not limited to: beta-lactams such as penicillins, cephalosporins, carbacephems, cephamycins, carbapenems, monobactams, quinolones including fluoroquinolones and similar DNA synthesis inhibitors, tetracyclines, aminoglycosides, macrolides, glycopeptides, chloramphenicols, glycylcyclines, lincosamides, lipopeptides, lipodepsipeptides, such as daptomycin, and oxazolidinones.

In some embodiments, the bacterial infection is an upper and lower respiratory tract infection, pneumonia, bacteremia, a systemic infection, sepsis and septic shock, a urinary tract infection, a gastrointestinal infection, endocarditis, a bone infection, central nervous system infections such as meningitis, or an infection of the skin and soft tissue. The disclosure includes a method of treating *C. difficile* by administering a dosage form of the disclosure to a patient in need of such treatment. The disclosure particularly includes a method of treating a complicated urinary tract infection in a patient. A "complicated urinary tract infection" is a clinical syndrome characterized by pyuria and a documented microbial pathogen on culture of urine blood, accompanied by local and systemic signs and symptoms, including fever (i.e., oral or tympanic temperature greater than 38 degrees Celsius), chills, malaise, flank pain, back pain, and/or costovertebral angle pain or tenderness, that occur in the presence of a functional or anatomical abnormality of the urinary tract or in the presence of catheterization. Patients with pyelonephritis, regardless of underlying abnormalities of the urinary tract, are considered a subset of patients with cUTIs.

In some embodiments, the subject is a mammal, e.g., a human or non-human mammal. In some embodiments, the methods include treating one or more cells, e.g., cells in a culture dish.

In one aspect, the present disclosure features a method of treating a Gram-negative infection in a subject, the method comprising administering to said subject in need of such treatment a therapeutically effective amount of a compound described herein.

In some embodiments, the Gram-negative infection is caused by *Pseudomonas aeruginosa*.

In other embodiments the disclosure includes treating an infection caused by Gram-positive bacteria, such as *Staphylococcus epidermidis* and *Staphylococcus aureus*.

In some embodiments, the subject is a trauma patient or a burn patient suffering from a burn or skin wound.

In a further aspect, the present disclosure features a method of reducing bacterial tolerance in a subject, the method comprising administering to said subject a therapeutically effective amount of a compound described herein.

In some embodiments, the method further includes identifying said subject suffering from an infection with bacteria resistant to antimicrobial therapy.

EXAMPLES

Tablet Manufacture

The tebipenem pivoxil tablets use a common blend that is manufactured via dry granulation such as roller compaction followed by milling. Conventional blending/milling and tableting equipment and processes are used. Conventional film coating equipment and processes can be used to coat the tablet cores.

Tebipenem pivoxil blends can be prepared by a variety of granulation processes, including spray drying, solvent wet granulation, aqueous wet granulation and dry granulation using roller compaction; however, dry granulation using roller compaction efficiently produces tebipenem pivoxil tablet blends with desirable bulk density and flow properties.

The manufacturing process of tebipenem pivoxil tablets is optimized through evaluation of blend and tablet physical properties including bulk and tap density measurement, flow analysis, screen analysis, and uniformity of the blend; weight, thickness, hardness, friability, potency, disintegration, dissolution and content uniformity tests on the tablet cores and tablets.

Example 1. Tebipenem Pivoxil Immediate Release Tablet Cores

Tebipenem pivoxil, crospovidone (PVPP XL-10), monohydrate lactose, and microcrystalline cellulose (Avicel PH102) are weighed and placed into a container. These ingredients are then sieved through a mesh 30 sieve.

The sieved ingredients are blended for 10 minutes at 20 rpm using a single arm fixed hopper mixing machine.

To the resulting mixture of the blended ingredients, magnesium stearate is added in the mixing machine, the mixture is further blended for 5 minutes at 20 rpm.

The mixture is compressed into tablets with 9 mm diameter round punches using single-punch tablet press.

Figure 1:
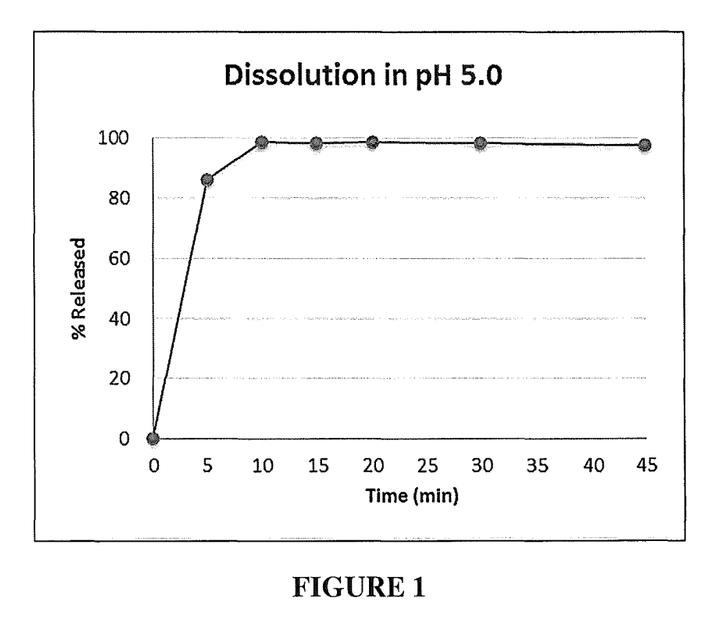
FIG. 1 shows a dissolution profile of a 500 mg immediate release tebipenem pivoxil uncoated tablet core at pH 5. The formulation of the tablet core is provided in Example 1.

The compositions of the 500 mg and 100 mg immediate release tablet cores are listed in Tables 1 and 2, respectively. The dissolution profile of the 500 mg immediate release tebipenem pivoxil tablet is at pH 5.0 is shown in FIG. 1.

TABLE 1

| Components | Function | Amount (%) | Quantity per 500 mg tablet (mg) |
|---|---|---|---|
| tebipenem pivoxil (free base) | Active | 50.0 | 500.0 |
| Crospovidone (PVPP XL-10) | Disintegrant | 5.0 | 50.0 |
| Monohydrate Lactose | Diluent | 21.5 | 215.0 |
| Microcrystalline cellulose (Avicel PH102) | Binder | 21.5 | 215.0 |
| Magnesium Stearate | Lubricant | 2.0 | 20.0 |
| Total | | 100.00 | 1,000 |

TABLE 2

| Components | Function | Amount (%) | Quantity per 100 mg tablet (mg) |
|---|---|---|---|
| tebipenem pivoxil (free base) | Active | 50.0 | 100.0 |
| Crospovidone (PVPP XL-10) | Disintegrant | 5.0 | 10.0 |
| Monohydrate Lactose | Diluent | 21.0 | 42.0 |
| Microcrystalline cellulose (Avicel PH102) | Binder | 21.0 | 42.0 |
| Magnesium Stearate | Lubricant | 2.0 | 4.0 |
| SiO$_2$ | Filler | 1.0 | 2.0 |
| Table Core Total | | 100.00 | 200 |
| Film Coating | (see below) | 7.0 | 14.0 |
| Tablet Weight | | 107.0 | 214.0 |

Example 2. Immediate Release Coating Formulation and Process

Figure 3:
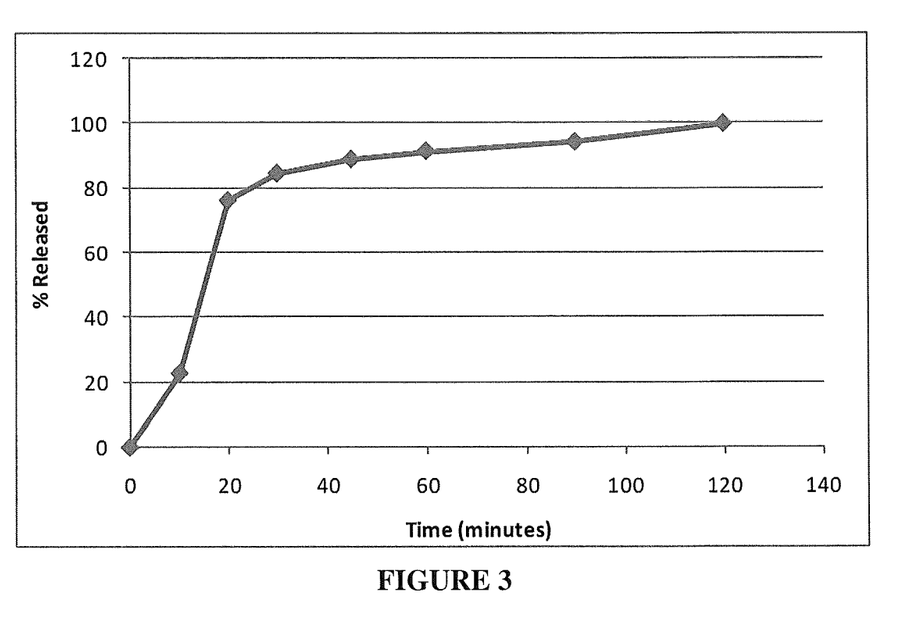
FIG. 3 shows the dissolution profiles of a 500 mg enteric coated immediate release tablet at pH 6.8. The composition of the tablet core is provided in Example 1 and the composition of the enteric coating is provided at Example 2, Table 3.

Immediate release tebipenem pivoxil table cores, such as those disclosed in Tables 1 and 2, can be coated with coating formulations listed in Tables 3 and 4. The dissolution profile of a 500 mg enteric coated immediate release tebipenem pivoxil is provided in FIG. 3. The formulation of the tablet core is provided in Example 1 and the formulation of the enteric coating is provided in Table 3. The resulting enteric coated dosage form can release 100% of the tebipenem pivoxil at pH 6.8 in 45 minutes, but releases less than 5% of the tebipenem pivoxil at pH 1.2 in 45 minutes. The following abbreviations are used: GMS (glycerol monostearate) and TEC (Triethyl citrate).

TABLE 3

| | Composition Ingredients (g) | |
|---|---|---|
| Eudragit Dispersion (a) | Eudragit L 100-55 | 225 |
| | Sodium hydroxide (aq) (4%) | 75 |
| | Water | 450 |
| | Total | 750 |

TABLE 4

| | Composition Ingredients (g) | |
|---|---|---|
| Eudragit Dispersion (b) | Eudragit dispersion(a) | 750 |
| | GMS | 11.25 |
| | TEC | 22.5 |
| | Tween 80 | 4.5 |
| | Water | 245 |
| | Total | 1033.25 |
| | Solid content | 22.9% |

The Eudragit Dispersion (a) is prepared as follows. Eudragit L100-55 is weighed and added slowly into the water under stirring that forms a vortex. The mixture is stirred for 10 minutes to make the polymer wet completely. An aqueous 4% sodium hydroxide solution is added during a 5 minute period to the resulting dispersion by drops, and the resulting mixture is further stirred for 30 minutes.

The Eudragit Dispersion (b) is prepared as follows. A mixture of Tween 80, TEC, and GMS is added to water heated to 80° C., and the resulting mixture was homogenized for 10 minutes at a speed of 5,000 rpm. Additional water (25% of the original amount) is added to the dispersion under stirring. The resulting mixture is cooled to ambient temperature. The prepared dispersion is then added to Eudragit Dispersion (a) prepared as described above under stirring. After 10 minutes of stirring, the resulting mixture is passed through a mesh 80 sieve. The resulting dispersion can be used to coat tebipenem pivoxil immediate release tablet cores (weight gain 7%) according to the parameters listed in Table 5. The dissolution profiles of uncoated tebipenem pivoxil immediate release tablet core (formulation in Example 1) and enteric coated tebipenem pivoxil.

TABLE 5

| | |
|---|---|
| Temperature (inlet) | 45-55° C. |
| Temperature (material) | 33-35° C. |
| Fan frequency (inlet) | 900 Hz |
| Fan frequency(outlet) | 1,500 Hz |
| Flow rate | 2-5 g/min |
| Atomization pressure | 2.5 bar |
| Pan speed | 7-15 rpm |

Example 3. Tebipenem Pivoxil Modified Release Tablet Core Composition

Modified release tebipenem pivoxil tablet cores of Tables 6 and 7 are manufactured as follows. First, a half portion of hydroxypropyl methyl cellulose (HPMC E50 LV) is charged into a blender, such as a V-blender or bin blender, followed by addition of tebipenem pivoxil and then the remaining half portion of hydroxypropyl methyl cellulose, and then blending the materials.

The magnesium stearate may be screened to break up any agglomerates such as through a 20 mesh screen. The screened magnesium stearate is added to the blender containing the tebipenem pivoxil/release control agent blend and blended for several minutes. The tebipenem pivoxil/release control agent/magnesium stearate blend from the blender is discharged.

The material discharged from the blender is roller compacted to form roller compacted ribbons or compacts. The roller compacted material is then passed through a mill, such as an oscillating mill, impact mill, or screening mill. For example, a QUADRO COMIL (Quadro Engineering, Ontario, Canada) equipped with a 20 mesh screen may be used. The milled material is collected and then charged into a blender. Microcrystalline cellulose (Avicel PH102) and mannitol (Mannitol 200 SD) are added and the materials are blended.

Magnesium stearate may be screened to break up any agglomerates such as through a 20 mesh screen into the blender and blended several minutes.

The contents of the blender are then discharged into an appropriately labeled container, double lined with polyethylene bags with a desiccant between the two layers of bags.

Tablet cores are then formed on a rotary tablet press. Tablet cores may be coated in a film coater.

The compositions of the 500 mg (total weight 1000 mg) and 100 mg (total weight 200 mg) modified release tablet cores are listed in Tables 6 and 7, respectively.

TABLE 6

| Components | Function | Amount (%) | Quantity per 1,000 mg tablet (mg) |
|---|---|---|---|
| tebipenem pivoxil | Active | 50.0 | 500.0 |
| HPMC E50 LV | Release Control Agent | 20.0 | 200.0 |
| Mannitol 200 SD | Diluent | 14.0 | 140.0 |

TABLE 6-continued

| Components | Function | Amount (%) | Quantity per 1,000 mg tablet (mg) |
|---|---|---|---|
| Microcrystalline cellulose (Avicel PH102) | Binder | 14.0 | 140.0 |
| Magnesium Stearate | Lubricant | 2.0 | 20.0 |
| Total | | 100.00 | 1,000 |

TABLE 7

| Components | Function | Amount (%) | Quantity per 200 mg tablet (mg) |
|---|---|---|---|
| tebipenem pivoxil (free base) | Active | 50.0 | 100.0 |
| HPMC E50 LV | Release Control Agent | 20.0 | 40.0 |
| Mannitol 200 SD | Diluent | 14.0 | 28.0 |
| Microcrystalline cellulose (Avicel PH102) | Binder | 14.0 | 28.0 |
| Magnesium Stearate | Lubricant | 1.0 | 2.0 |
| $SiO_2$ | Filler | 1.0 | 2.0 |
| Total | | 100.00 | 200 |

The tablet was prepared by a direct compression. The tooling size was 18.9 by 11.0 mm. The thickness of the tablet was 6.83 to 6.90 mm.

Example 4. Dissolution

The dissolution method parameters are listed in Table 8.

TABLE 8

| | |
|---|---|
| Drug Product/Formulation | tebipenem pivoxil Tablet: 1,000 mg total core weight API: 500 mg |
| Dissolution Media | pH 5.0 acetate buffer |
| Media size | 900 mL |
| Replacement Volume | 5 mL |
| Paddle speed | 50 rpm (3-4 h, 200 rpm) |
| Sampling Time Points | 0.5, 1, 2, 3, and 4 h |
| Diluent for Standard | pH 5.0 buffer solution |
| Standard Concentration | 100 μg/mL |
| Sample concentration range | 11.11-111.11 μg/mL (10%-100% of drug release) |
| Column | Welch Ultisil, XB-C18, 250 mm × 4.6 mm, 5 μm; Lot No. 2101.102; Part# 00210-31043; Serial# 211603926 |
| Mobile Phase | 50 mM Ammonium Acetate/Acetonitrile/Triethylamine (58:40:2, v/v/v), pH 3.5 (adjusted by phosphoric acid) |
| Flow Rate, mL/min | 0.8 |
| UV Wavelength, nm | 330 |
| Injection volume, μL | 10 |
| Column Temperature, ° C. | 25 |
| Autosampler Temp, ° C. | RT |
| Run Time, min | 7 |

Example 5. Simulated Human Tebipenem Pivoxil Pharmacokinetic Parameters for Immediate Release Dosage Form The pharmacokinetic parameters shown in Tables 9 and 10 were obtained from a simulated study of the human orally-administered (PO) dose of the 500 mg immediate release tebipenem pivoxil tablet. The formulation of this tablet core is provided in Example 1. The simulation assumes that in vivo dissolution of Tebipenem Pivoxil tablet is similar to the measured in vitro dissolution.

Figure 4:
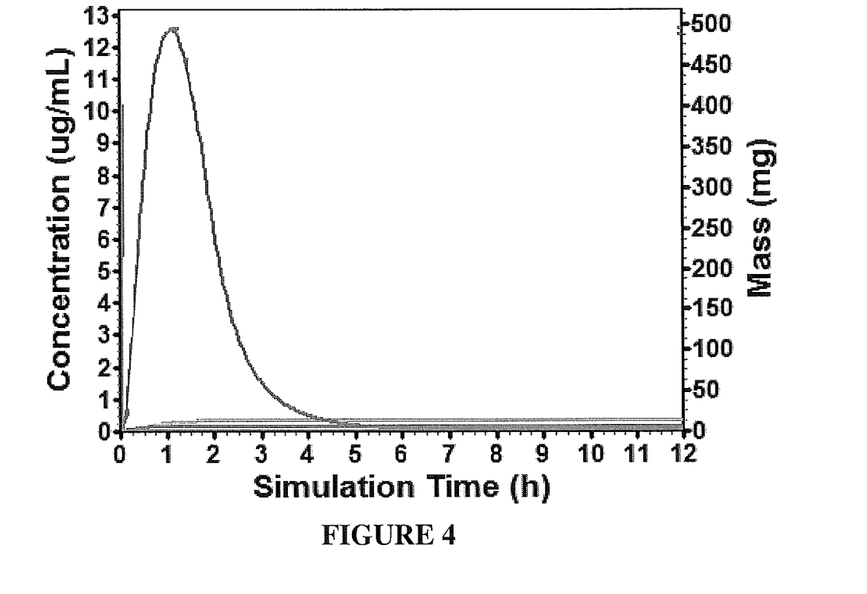
FIG. 4 is a graph of concentration (milligrams per liter, ug/mL) and mass (milligrams, mg) versus simulation time (hours, h). The graph is a simulated pharmacokinetic profile of the human orally-administered (PO) dose of a 500 mg tebipenem pivoxil tablet.

The simulated pharmacokinetic profile of the human orally-administered (PO) dose of 500 mg Tebipenem Pivoxil tablet is shown in FIG. 4. The simulation shows the plasma concentration of tebipenem (free form) in the venous return, i.e. the plasma concentration of tebipenem in the venous compartment or systemic circulation.

TABLE 9

| Time (hours) | Amount Dissolved (%) |
|---|---|
| 0.08 | 86.4 |
| 0.17 | 98.7 |
| 0.25 | 98.5 |
| 0.33 | 98.9 |
| 0.50 | 98.6 |
| 0.75 | 97.7 |

TABLE 10

| $C_{max}$ (µg/mL) | $AUC_{0-12}$ (µg · h/mL) | $AUC_{0-inf}$ (µg · h/mL) | $C_6$ (pg/mL) | $C_{12}$ (pg/mL) |
|---|---|---|---|---|
| 12.54 | 22.20 | 22.58 | 0.087 | 0.031 |

Example 6. Immediate Release Tebipenem Pivoxil HBr Tablets

Immediate release tebipenem pivoxil HBr tablets are manufactured by the method given in Example 1. Tebipenem pivoxil free base is substituted by the HBr salt. Less lactose and Avicel PH102 is used to account for the greater weight of the tebipenem pivoxil salt. The composition of uncoated immediate release tebipenem pivoxil HBr tablets is given in Tables 11A and 11B. The 750 mg (total weight) tablet core disclosed in Table 11B was found to release 95.0% of the tebipenem pivoxil in 5 minutes, and approximately 95.2% of the tebipenem pivoxil in 15 minutes when measured by the USP Paddle method at 50 rpm in 900 mL of 50 mM acetate buffer, pH 5.0 at 37° C. The dissolution profile is provided at FIG. 7. The tablet core in Table 11B contains 300 mg tebipenem pivoxil.

TABLE 11A

| Components | Function | Amount (%) | Quantity per 100 mg tablet (mg) |
|---|---|---|---|
| tebipenem pivoxil HBr | Active | 58.2 | 116.3 |
| Crospovidone (PVPP XL-10) | Disintegrant | 5.0 | 10.0 |
| Monohydrate Lactose | Diluent | 16.9 | 33.8 |
| Microcrystalline cellulose (Avicel PH102) | Binder | 17.0 | 42.0 |
| Magnesium Stearate | Lubricant | 2.0 | 4.0 |
| $SiO_2$ | Filler | 1.0 | 2.0 |
| Table Core Total | | 100.00 | 200 |

TABLE 11B

| Components | Function | Amount (%) | Quantity per 300 mg tablet (750 total weight) |
|---|---|---|---|
| tebipenem pivoxil HBr | Active | 46.5 (40% free base) | 348.9 |
| PVPP XL-10 (crospovidone) | Disintegrant | 5.0 | 37.5 |
| Mannitol 200 SD | Diluent | 23.2 | 174.3 |
| Microcrystalline cellulose (Avicel PH102) | Binder | 23.2 | 174.3 |
| Magnesium Stearate | Lubricant | 1.0 | 7.5 |
| $SiO_2$ | Filler | 1.0 | 7.5 |
| Total | | 100.0 | 750.0 |

Example 7. Modified Release Tebipenem Pivoxil HBr Tablets

Figure 5:
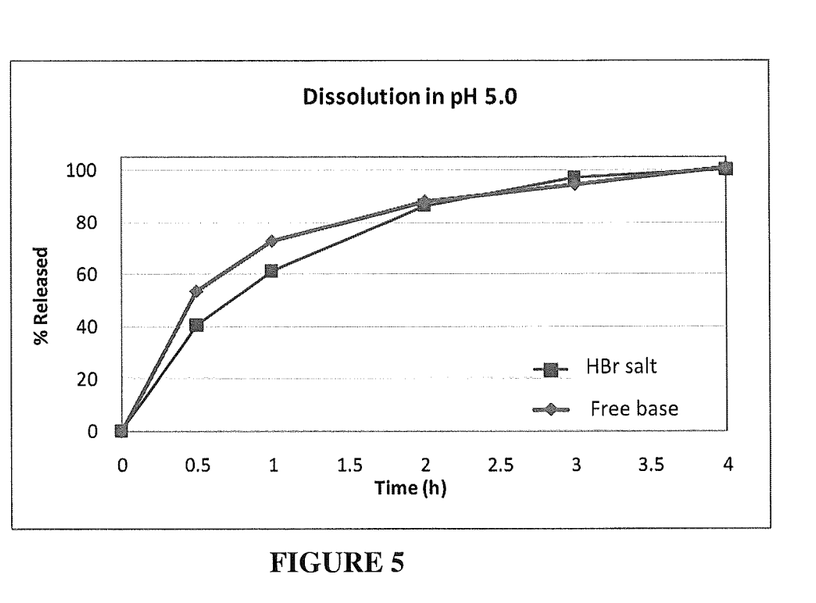
FIG. 5 is a comparison of the dissolution profiles of the modified release tebipenem pivoxil HBr salt (Table 12A) and modified release tebipenem pivoxil free base (Table 7) at pH 5.0.
Figure 6:
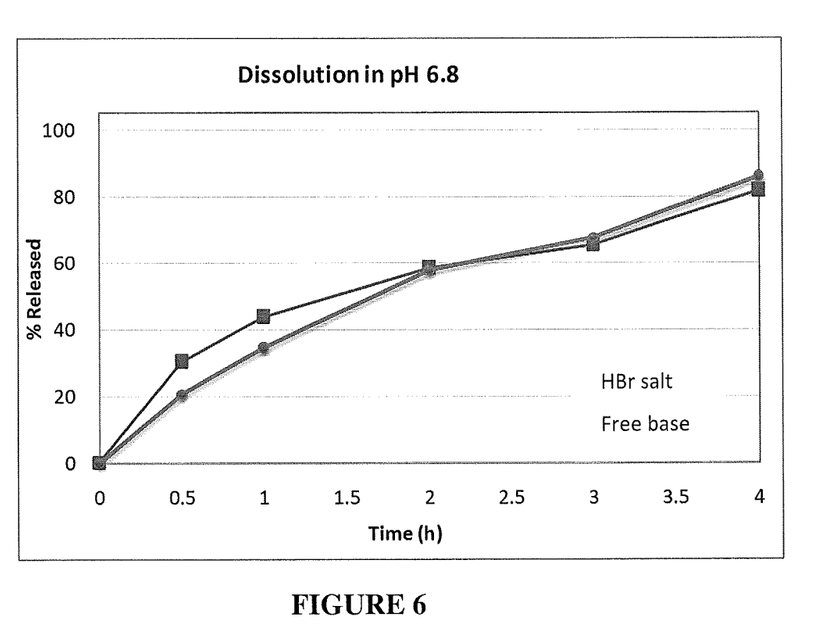
FIG. 6 is a comparison of the dissolution profiles of the modified release tebipenem pivoxil HBr salt (Table 12A) and modified release tebipenem pivoxil free base (Table 7) at pH 6.8.

Modified release tebipenem pivoxil HBr tablets are manufactured by the method given in Example 2. Tebipenem pivoxil free base is substituted by the HBr salt. Less lactose and Avicel PH102 is used to account for the greater weight of the tebipenem pivoxil salt. The composition of examples of uncoated modified release tebipenem pivoxil HBr tablets is given in Tables 12A and 12 B. The dissolution profile of the uncoated modified release tebipenem pivoxil tablet in Table 12A at pH 5.0 and pH 6.8 is compared to that of the free base in FIG. 5 and FIG. 6. The HBr salt exhibited a slightly slower release than the free base at pH 5.0 and a slightly faster release than the free base at pH 6.8.

TABLE 12A

| Components | Function | Amount (%) | Quantity per 200 mg tablet (mg) |
|---|---|---|---|
| tebipenem pivoxil HBr | Active | 58.2 | 116.3 |
| HPMC K4M | Release Control Agent | 20.0 | 40.0 |
| Mannitol 200 SD | Diluent | 14.0 | 19.9 |
| Microcrystalline cellulose (Avicel PH102) | Binder | 14.0 | 19.8 |
| Magnesium Stearate | Lubricant | 1.0 | 2.0 |
| $SiO_2$ | Filler | 1.0 | 2.0 |
| Total | | 100.00 | 200.00 |

TABLE 12B

| Components | Function | Amount (%) | Quantity per 300 mg tablet (750 total weight) |
|---|---|---|---|
| tebipenem pivoxil HBr | Active | 46.5 (40% free base) | 348.9 |
| HPMC E3 | Release Control Agent | 35.0 | 262.5 |
| Mannitol 200 SD | Diluent | 8.2 | 61.8 |
| Microcrystalline cellulose (Avicel PH102) | Binder | 8.2 | 61.8 |
| Magnesium Stearate | Lubricant | 1.0 | 7.5 |
| $SiO_2$ | Filler | 1.0 | 7.5 |
| Total | | 100.00 | 750.0 |

The 750 mg tablet core disclosed in Table 12B was found to release 21.9% of the tebipenem pivoxil in 30 minutes, 40.9% of the tebipenem pivoxil in 1 hour, 70.7% of the of the tebipenem pivoxil in 2 hours, 88.7% of the tebipenem pivoxil in 3 hours, and 100% of the of the tebipenem pivoxil in 4 hours when measured by the USP Paddle method at 50 rpm in 900 mL of 50 mM acetate buffer, pH 5.0 at 37° C. The dissolution profile is provided at FIG. 8.

Example 8. Short Modified Release Tebipenem Pivoxil HBr Formulation

Figure 9:
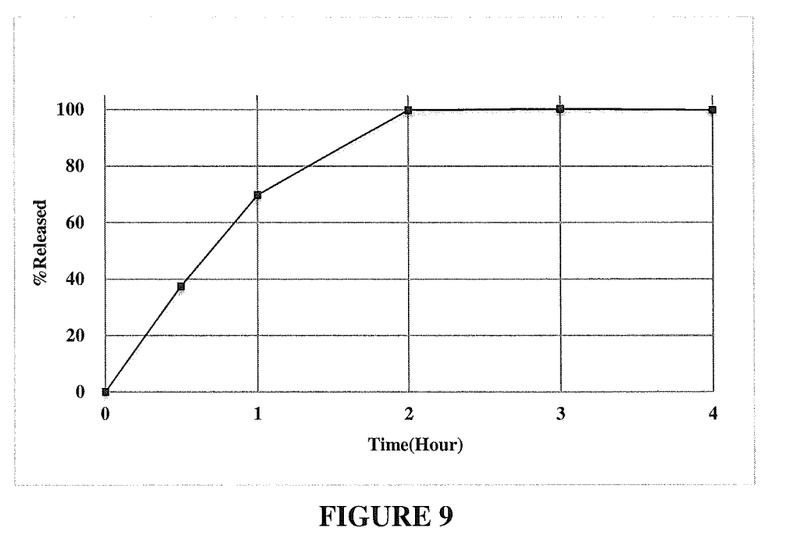
FIG. 9 shows a dissolution profile of a 300 mg tebipenem pivoxil short modified release uncoated tablet core at pH 5. The formulation of the modified release dosage form is provided in Table 13.

Short modified release tebipenem pivoxil HBr tablets are manufactured by the method given in Example 2. This formulation releases NLT 85% of the tebipenem pivoxil from the dosage form core in 2 hours when measured by the USP Paddle method at 50 rpm in 900 mL of 50 mM acetate buffer, pH 5.0 at 37° C. Tebipenem pivoxil free base is substituted by the HBr salt. The composition of examples of uncoated modified release tebipenem pivoxil HBr tablets is given in Table 13. The 750 mg tablet core disclosed in Table 13 was found to release 37.5% of the tebipenem pivoxil in 30 minutes, 69.8% of the tebipenem pivoxil in 1 hour, 99.9% of the of the tebipenem pivoxil in 2 hours, and 100.0% of the tebipenem pivoxil in 3 hours when measured by the USP Paddle method at 50 rpm in 900 mL of 50 mM acetate buffer, pH 5.0 at 37° C. The dissolution profile of the short modified release tebipenem pivoxil HBr tables is given in FIG. 9.

TABLE 13

| Components | Function | Amount (%) | Quantity per 300 mg tablet (750 total weight) |
|---|---|---|---|
| tebipenem pivoxil HBr | Active | 46.5 (40% free base) | 348.9 |
| PVP K12 | Release Control Agent | 30.0 | 225.0 |
| Mannitol 200 SD | Diluent | 10.7 | 80.5 |
| Microcrystalline cellulose (Avicel PH102) | Binder | 10.7 | 80.6 |
| Magnesium Stearate | Lubricant | 1.0 | 7.5 |
| $SiO_2$ | Filler | 1.0 | 7.5 |
| Total | | 100.00 | 750.0 |

Example 9. PK Parameters for Oral Administration to Monkeys

The 100 mg immediate release tebipenem pivoxil free base (Free Base IR) and HBr (HBr IR) tablets Examples 1 and 6 and the 100 mg modified release tebipenem pivoxil HBr tablet of Example 7 (HBr MR) were orally administered to Cynomolgus monkeys (N=4 animals/tested dosage form). Each animal received a one week wash out prior to the next dose and each served as its own control. Blood samples were collected into $K_2EDTA$ tubes before processing to plasma. Samples were obtained at 15 minutes, 30 minutes, 1 hours, 2 hours, 4 hours, 6 hours, 8 hours, 10 hours, 12 hours, 16 hours, and 24 hours post administration. Plasma samples were analyzed for the prodrug, tebipenem pivoxil, and tebipenem via a tandem LC-MS method. Non-compartmental analysis used to derive pharmacokinetic parameters of the composite time vs. concentration profiles were performed for each dose level using Phoenix Winnonlin v. 6.4. Plasma concentration of tebipenem for each time point was determined by HPLC. The PK parameters for the immediate release and extended release dosage forms are listed in Table 14.

Maximal concentrations of tebipenem were observed at approximately 1.5-2 hours in the free base and HBr immediate release groups. $C_{max}$ was reduced with the modified release formulation compared to the immediate release (free base and HBr) formulation but $AUC_{all}$ was relatively constant between the formulations. $AUC_{inf}$ could not be calculated due to the variability in the terminal elimination profile. Using previously generated IV data (13.06 ug*hr/mL for 10 mg/kg dose) bioavailability of tebipenem was estimated to range 39-50%. Mean residence time was increased in the extended release formulation.

TABLE 14

| Dosage Form | $MRT_{last}$ (hr) | | $T_{max}$ (hr) | | $C_{max}$ (µg/mL) | | C12 h (µg/mL) | | AUC (hr* µg/mL) | |
|---|---|---|---|---|---|---|---|---|---|---|
| | Mean | SD | Mean | SD | Mean | SD | Mean | SD | Mean | SD |
| Free Base IR | 1.89 | 1.0 | 1.63 | 1.6 | 12.2 | 9.2 | 0.0393 | NA | 17.5 | 5.4 |
| HBr IR | 1.55 | 0.82 | 1.0 | 0.0 | 13.6 | 9.2 | 0.0178 | NA | 19.1 | 6.2 |
| HBr MR (4 hr) | 2.86 | 1.3 | 2.25 | 1.3 | 6.04 | 4 | | | 14.4 | 5.5 |

The present inventive concept has been described in terms of exemplified principles and embodiments, but those skilled in the art will recognize that variations may be made and equivalents substituted for what is described without departing from the scope and spirit of the disclosure as defined by the following claims.

What is claimed is:

1. A tebipenem pivoxil HBr tablet core comprising at least 60% (w/w) tebipenem pivoxil, wherein tebipenem is the only therapeutic active agent.

2. The tebipenem pivoxil HBr tablet core of claim 1, comprising a binder and a disintegrant.

3. The tebipenem pivoxil HBr tablet core of claim 2, wherein the tablet core additionally comprises a lubricant.

4. A method of treating a bacterial infection in a subject, comprising administering a dosage form comprising a tablet core of claim 1 to the subject, wherein the subject is at risk for the bacterial infection or is suffering from the bacterial infection.

5. The tebipenem pivoxil HBr dosage form of claim 1, wherein the tablet core comprises 300 mg tebipenem pivoxil.

6. The tebipenem pivoxil HBr tablet core of claim 2, wherein the binder is microcrystalline cellulose, silicified microcrystalline cellulose, ethyl cellulose, lactose, or any combination of any two or more of the foregoing.

7. The tebipenem pivoxil HBr tablet core of claim 2, wherein the disintegrant is croscarmellose sodium, crospovidone, sodium starch glycolate, or any combination of any two or more of the foregoing.

8. The tebipenem pivoxil HBr tablet core of claim 2, wherein the binder is microcrystalline cellulose and the disintegrant is crospovidone.

9. The method of claim 4, wherein the bacterial infection is a urinary tract infection, a complicated urinary tract infection, or pyelonephritis.

10. The method of claim 4, wherein the bacterial infection is a urinary tract infection, a complicated urinary tract infection, or pyelonephritis.

11. A method of treating pyelonephritis in a subject, comprising administering a dosage form comprising a tablet core of claim 1 to the subject, wherein the subject is at risk for the pyelonephritis or is suffering from pyelonephritis.

12. A method of treating a complicated urinary tract infection in a subject, comprising administering a dosage form comprising a tablet core of claim 1 to the subject, wherein the subject is at risk for the complicated urinary tract infection or is suffering from the complicated urinary tract infection.

13. The tebipenem pivoxil HBr tablet core of claim 1, comprising at least 65% (w/w) tebipenem pivoxil.

14. The tebipenem pivoxil HBr tablet core of claim 1, wherein the tablet core comprises:
- a binder, wherein the binder is or comprises microcrystalline cellulose or silicified microcrystalline cellulose;
- a disintegrant, wherein the disintegrant is or comprises crospovidone; and
- a lubricant, wherein the lubricant is or comprises magnesium stearate.

15. The tebipenem pivoxil HBr tablet core of claim 1, wherein the tablet core is coated.

16. The tebipenem pivoxil HBr tablet core of claim 14, wherein the tablet core is coated with an immediate release coating.

* * * * *